US011925343B2

United States Patent
Ji et al.

(10) Patent No.: US 11,925,343 B2
(45) Date of Patent: Mar. 12, 2024

(54) TRACTION APPARATUS AND TRACTION RING FOR TRACTION APPARATUS (71) Applicants: MICRO-TECH (NANJING) CO., LTD., Jiangsu (CN); BEIJING FRIENDSHIP HOSPITAL, CAPITAL MEDICAL UNIVERSITY, Beijing (CN)

(72) Inventors: Ming Ji, Beijing (CN); Jianjun Shuang, Jiangsu (CN); Zhenghua Shen, Jiangsu (CN); Changging Li, Jiangsu (CN); Derong Leng, Jiangsu (CN); Chunjun Liu, Jiangsu (CN); Jie Hu, Jianbosu (CN)

(73) Assignees: MICRO-TECH (NANJING) CO., LTD., Jiangsu (CN); BEIJING FRIENDSHIP HOSPITAL, CAPITAL MEDICAL UNIVERSITY, Beijing (CN)

( * ) Notice: Subject to any disclaimer, the term of this patent is extended or adjusted under 35 U.S.C. 154(b) by 527 days.

(21) Appl. No.: 17/089,369

(22) Filed: Nov. 4, 2020

(65) Prior Publication Data
US 2021/0068805 A1    Mar. 11, 2021

Related U.S. Application Data (63) Continuation-in-part of application No. PCT/CN2019/096455, filed on Jul. 18, 2019.

(30) Foreign Application Priority Data

Jul. 20, 2018 (CN) .......................... 201810800013.5

(51) Int. Cl.
*A61B 17/02* (2006.01)
*A61B 17/00* (2006.01)
(52) U.S. Cl.
CPC .... *A61B 17/0293* (2013.01); *A61B 17/00234* (2013.01); *A61B 17/0206* (2013.01);
(Continued)

(58) Field of Classification Search
CPC . A61B 17/02; A61B 17/0281; A61B 17/0293; A61B 2017/0225; A61B 2017/0212; A61B 2017/0287
See application file for complete search history.

(56) References Cited

U.S. PATENT DOCUMENTS 5,972,022 A * 10/1999 Huxel ................... A61F 2/0063
606/215
9,463,003 B2 * 10/2016 Gordin ............. A61B 17/00234
(Continued)

FOREIGN PATENT DOCUMENTS

CN        202044337 U     11/2011
CN        106037838 A     10/2016
(Continued)

OTHER PUBLICATIONS

Chen et al., A Clinical Comparative Study of Rubber Ring versus Dental Floss Combined with Hemoclipping Assisted Endoscopic Submucosal Dissection on Gastrointestinal Tumor), Journal of Shanghai Jiaotong University (Medical Science (Jul. 31, 2017), 37(7):1010-1014 (see English abstract).

*Primary Examiner* — Eduardo C Robert
*Assistant Examiner* — Michelle C Eckman
(74) *Attorney, Agent, or Firm* — K&L Gates LLP (57) ABSTRACT

A traction apparatus, comprising a clip portion (2) and a traction portion (1), the traction portion containing a closed traction structure (11); the closed traction structure being made from an elastic material; the clip portion comprising a main clip body (23, 25) and a clip arm (24, 26); the main clip body being capable of passing through a biopsy channel (4) of an endoscope (3), the clip arm being capable of clip the closed traction structure. Also disclosed is a traction ring used for the traction apparatus, the traction ring being a single closed traction structure or being formed by connecting several closed traction structures, the traction ring being made from an elastic material.

18 Claims, 6 Drawing Sheets

(52) U.S. Cl.
CPC ............ *A61B 2017/00269* (2013.01); *A61B 2017/00862* (2013.01); *A61B 2017/0287* (2013.01)

(56) References Cited

U.S. PATENT DOCUMENTS

| | | | |
|---|---|---|---|
| 2007/0250116 A1* | 10/2007 | Raju | A61B 17/0218 606/216 |
| 2009/0221934 A1 | 9/2009 | Kuhns et al. | |
| 2010/0174150 A1* | 7/2010 | Park | A61B 17/0218 600/218 |
| 2013/0053745 A1 | 2/2013 | Kobayashi et al. | |
| 2017/0209132 A1 | 7/2017 | Bhatt et al. | |
| 2019/0099172 A1* | 4/2019 | Wales | A61B 1/018 |
| 2020/0360006 A1* | 11/2020 | Sluti | A61B 17/0218 |

FOREIGN PATENT DOCUMENTS

| | | |
|---|---|---|
| CN | 107361804 A | 11/2017 |
| CN | 208625767 U | 3/2019 |
| WO | 2007101463 A1 | 9/2007 |
| WO | 2019066084 A1 | 4/2019 |

* cited by examiner

TRACTION APPARATUS AND TRACTION RING FOR TRACTION APPARATUS

CROSS-REFERENCE TO RELATED APPLICATIONS

This application is a continuation-in-part of PCT Application Serial No. PCT/CN2019/096455, filed Jul. 18, 2019, entitled TRACTION APPARATUS AND TRACTION RING FOR TRACTION APPARATUS, and which claims priority to Chinese Provisional Application No. 201810800013.5, which was filed on Jul. 20, 2018. The contents of each are incorporated by reference into this specification.

FIELD OF THE INVENTION

The present invention relates to a traction apparatus and a traction ring for the traction apparatus in the field of medical appliances, and in particular, to a traction apparatus that has better elasticity and may draw a nidus to be cut merely based on elastic force of a traction portion without external force, through which a visual field for an operation is fully exposed and a large wound surface may be drawn and reduced, so as to facilitate further closure of the wound surface.

BACKGROUND OF THE INVENTION

Treating early gastric cancer by using endoscopic mucosal resection (EMR) is clinically first used in Japan. Before EMR is brought in Japan, gastrectomy is the only way for treating the early gastric cancer. At present, this treatment method has been widely applied. Endoscopic submucosal dissection (ESD) refers to dissecting mucosa directly from submucosa under an endoscope by using an improved needle knife, and is evolved from EMR. Due to its high rate of complete resection and good safety. ESD is applied for early digestive cancer and other tumor resection, and has gradually become a widely accepted minimally invasive surgical treatment.

Both ESD and EMR achieve resection of a lesion by using a normal single-channel endoscope, avoiding the pain of laparotomy and organ removal. A disadvantage of EMR is that this technology cannot entirely excise a relatively large lesion, and therefore it is difficult to perform detailed pathological analyses on a fragment-shaped specimen, cancer stages cannot be clearly determined, and there is a relatively high risk of tumor recurrence. Moreover, compared with the laparotomy, the conventional EMR, and other endoscopic treatments, ESD has the advantages that the wound is small and the patient may be treated for multiple times at a plurality of sites, so that the doctor is enabled to obtain an entire pathological specimen of a tissue for analysis and the tumor with a relatively large area and an irregular form or is combined with an ulcer or a scar may be resected at a rate of greater than 96% to reduce the recurrence rate.

However, compared with EMR. ESD has long operation time, has a high risk, and is difficult to be operated. For example, operation time of EMR is about 20 minutes, while operation time of ESD is 60-90 mins. ESD has complications such as bleeding, perforation, a stricture, a postoperative infection etc., which is unfavorable for promotion and applications. Main steps of an ESD operation are: marking, submucosal injection, edge cutting, dissection and wound surface processing etc. For some cases of treating a nidus at a part where it is difficult to perform ESD, usually submucosal injections are repeatedly performed to provide a surgical field in the subsequent dissection operation. However, repeated injections may prolong operation time and increase risks of bleeding and perforation. Also, a body position of the patient may be adjusted according to the gravitational direction, so that a dissected surface obtains ideal tensile force and a surgical field is provided. However, in the operation (such as an operation for upper gastrointestinal tract), body positions for the patient to select are limited, which limits the surgical effect.

SUMMARY OF THE INVENTION

The present invention provides a traction apparatus and a traction ring for the traction apparatus, with which a nidus to be cut may be drawn merely based on elastic force of a traction portion without external force, and a visual field for an operation is fully exposed; at the same time, a large wound surface may be drawn and reduced, so as to facilitate further closure of the wound surface.

A traction apparatus according to the present invention includes a clip portion and a traction portion. Based on own elastic force, the traction portion has elastic deformation to provide traction force within the body to stretch a nidus, thus fully exposing the visual field for an operation. Because no external force is required, the traction apparatus may not be limited by the anatomical position and the size of an alimentary canal, may stretch mucosa, a tissue, or an organ, and is particularly suitable for positions at which it is difficult to perform an ESD operation. Therefore, a doctor is enabled to perform a mucosa dissection operation more intuitively and visibly. In this way, the operation may be more safe and simpler, operation time may be shortened, and pain of a patient may be relieved, thus being suitable for dissection of a large-area nidus.

Ina first aspect, the present application provides a traction apparatus, which includes a clip portion and a traction portion; the traction portion contains a closed traction structure; the closed traction structure is made of an elastic material; the clip portion includes a main clip body and clip arms; the main clip body can pass through a biopsy channel of an endoscope; and the clip arms can clip the closed traction structure. The endoscope includes a biopsy channel, an objective lens, an LED light source, a water inlet channel, a water outlet channel, and the like. The biopsy channel is configured to feed into a clip portion and a traction portion.

Preferably, the closed traction structure is made of silicon rubber or a thermoplastic elastomer.

Preferably, there are one, two, or more closed traction structures.

Preferably, the closed traction structure is a combination of one or more of round shape, triangular shape, rhombic shape, or square shape.

Preferably, an elastic structure is connected between two or more closed traction structures, and the elastic structure is an elastic linear structure, an elastic ring, or another structure.

The clip portion may be connected with the traction portion, and by moving the main clip portion after connecting, a traction force may be applied at two ends of the traction portion or in multiple directions, so that the closed traction structure can be deformed elastically.

In a second aspect, the present application provides a traction ring used for a traction apparatus, wherein the traction ring is a single closed traction structure or is formed by connecting a plurality of closed traction structures, the traction ring is made of an elastic material, and an elastic structure is connected between the closed traction structures.

Preferably, the elastic structure is an elastic linear structure, for example, an elastic ring, etc.

Preferably, the closed traction structure may be a combination of one or more of is round shape, triangular shape, rhombic shape, or square shape.

During an actual operation process, the mucosa is pre-separated within the body, and marks may be made around a position having a lesion by using an electric knife. Though the electric knife or by injecting through an external syringe, a pathological tissue swells, and a liquid buffer layer, that is, a "water cushion", is formed under the mucosa. The "water cushion" isolates a muscular layer and the tissue having a lesion, and meanwhile, prevents heat conduction. In this way, a surgical field becomes clearer, and a blood vessel is squeezed by the water cushion to be closed, thereby reducing a risk of bleeding. After the mucosa is pre-separated within the body, the electric knife is taken out, and a first clip portion of the traction apparatus is enabled. One end of the closed traction structure is clipped by a clip arm of the first clip portion. After the first clip portion and the closed traction structure are placed in the biopsy channel of the endoscope and reach a distal end of the biopsy channel, by observing from an eye lens of the endoscope, the clip arm of the first clip portion is opened to clip one end of a pre-separated tissue and one end of the closed traction structure. At this time, a proximal end and a distal end of the main clip body of the first clip portion are separated, so that the distal end of the main clip body of the first clip portion and the closed traction structure are left in the body.

The clipping operations are repeated, and a second clip portion is placed in the biopsy channel of the endoscope. After the distal end of the biopsy channel is reached, by observing from the eye lens of the endoscope, clip arms of the second clip portion are opened to pass through the other end of the closed traction structure. Move the clip arms to the other end of the pre-separated tissue and clip the edge of the pre-separated tissue under the guidance of the endoscope. Subsequently, a proximal end and a distal end of the main clip body of the second clip portion are separated, so that the distal end of the main clip body of the second clip portion and the closed traction structure are left in the body.

Because the closed traction structure is elastic, during a cutting process of an operation, a cut nidus is everted due to elastic force of the traction portion. With progress of a cutting operation, the cut nidus is constantly pulled up to be gradually separated from the muscular layer, until being completely pulled up. In this way, the nidus separation is completed. According to such a manner, the nidus is cut and is everted at the same time, thereby widening the surgical field. A blood vessel under a target to be cut may be found when looking directly from the endoscope, and bleeding caused by cutting the blood vessels may be avoided. In this way, the operation becomes more convenient and safer, and the operation time is shortened. If the nidus is too large, the number of clip portions and closed traction structures may be increased, so that the cut nidus is completely pulled up in multiple directions. Or a traction portion in an elastic linear structure may be selected, so that a range of elastic deformation of the entire traction portion is increased, and a nidus with a relatively large area is stretched.

According to the traction apparatus in the present application, the clip portion and the traction portion are combined as an integral; and the traction portion thereof is elastic, and may extend to provide acting force within the body. Because no external force is required, the traction apparatus may not be limited by the anatomical position and the size of the alimentary canal, and is particularly suitable for positions at which it is difficult to perform an ESD operation. Moreover, a range for stretching may be adjusted according to requirements, satisfying requirements for cutting niduses with different sizes. A visual field for the ESD operation is widened, the speed of the ESD operation is improved, and the operation time is saved.

During actual use of the traction apparatus, if it is found that traction is loosen, the number of the clip portions may be further added to clip the closed traction structure. Stretching towards other directions is performed, and then clip to close is performed to form a polygonal structure. In this way, traction force may be continued to be provided, and the visual field for the operation is widened, until the tissue is completely separated, so that the separation process is successfully performed.

LIST OF REFERENCE NUMBERS

1 Traction portion
11 Closed traction structure
12 Connection ring
2 Clip portion
21 First clip portion
22 Second clip portion
23 Main clip body
24 Clip arm
25 Main clip body
26 Clip arm
27 Inner thorn
3 Endoscope 4 Biopsy channel
5 Nidus
6 Mucosa layer
7 Muscular layer
8 Mucosa layer at an opposite side of a lumina

DETAILED DESCRIPTION OF THE EMBODIMENTS

To make objectives, technical solutions, and advantages of the present application clearer, the present application is further described in detail below with reference to the accompanying drawings and the embodiments. It should be understood that the specific embodiments described herein are merely used to explain the present application, and are not used to limit the present application.

In the following, the end of the endoscope that is close to the operator is defined as the proximal end, and the end far away from the operator is defined as the distal end.

Figure 1A:
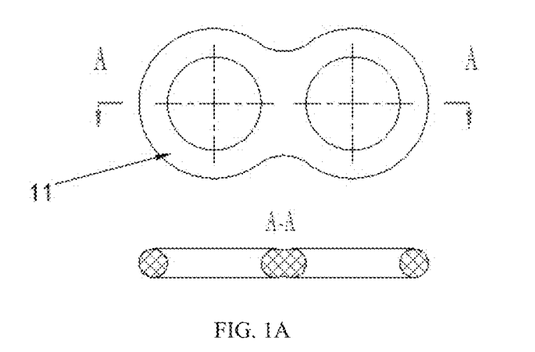
FIG. 1A is a sectional view and a front view of a traction portion including two annular closed traction structures.
Figure 1B:
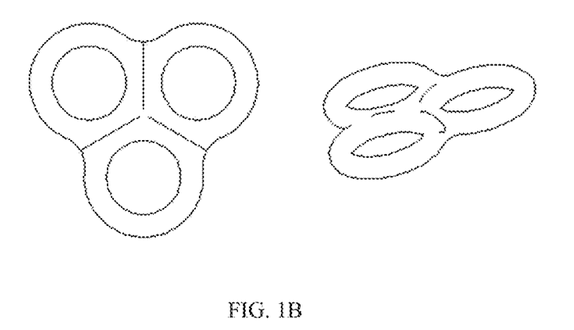
FIG. 1B is a schematic diagram of a traction portion including three annular closed traction structures.
Figure 1C:
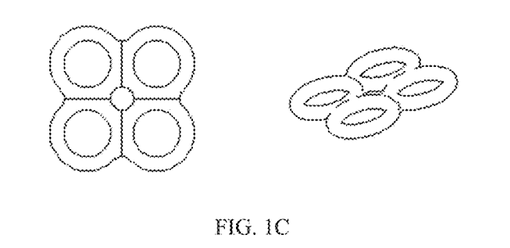
FIG. 1C is a schematic diagram of a traction portion including four annular closed traction structures.
Figure 1D:
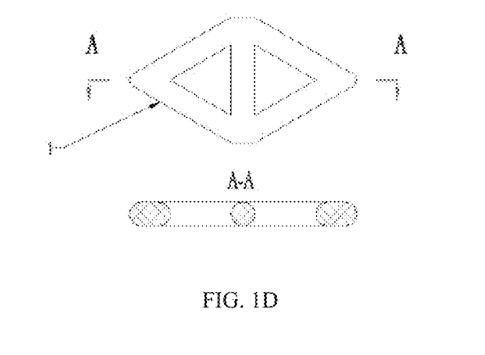
FIG. 1D is a sectional view and a front view of a triangular closed traction structure.
Figure 2:
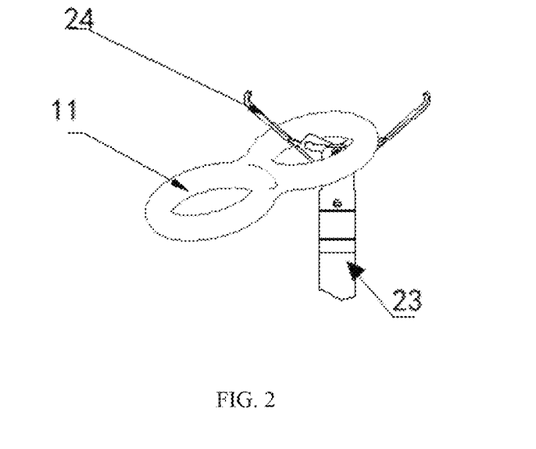
FIG. 2 is a schematic diagram showing cooperating of a clip portion and a traction portion with each other.
Figure 8:
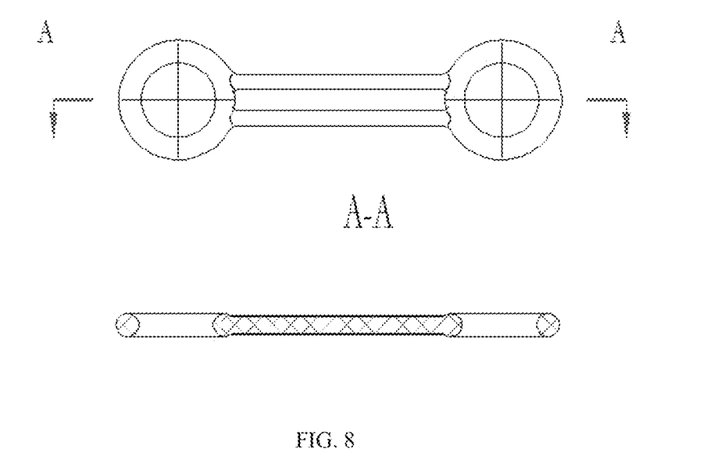
FIG. 8 is a schematic diagram of connecting an elastic linear structure between annular closed traction structures.

FIG. 1A to FIG. 1D and FIG. 8 are schematic diagrams of different types of closed traction structures. FIG. 1A is a schematic diagram of a traction portion 1 including two annular closed traction structures, wherein two annular structures are connected in a closed manner to form a traction portion 1 with a closed traction structure. FIG. 1B and FIG. 1C are schematic diagrams of a traction portion 1 including three annular closed traction structures and four annular closed traction structures. FIG. 1D is a sectional view and a front view of a triangular closed traction structure. As shown in FIG. 8, the traction portion 1 may also be mounted with an elastic linear structure in the closed traction structure. Both the closed traction structure and the elastic linear structure may have elastic deformation, so that a nidus 5 is completely separated from a mucosa layer 6. Such a structure is particularly suitable for a case in which the nidus 5 is relatively large. A closed traction structure 11 may be made of an elastic material. The elastic material may be silicon rubber or a thermoplastic elastomer. There may be one, two, or more closed traction structures. During actual use, according to different sizes of niduses, different types of traction portions may be selected to conduct the stretching and separating, being suitable for the traction operations of a mucosa, a tissue, an organ, and the like.

In the following, an operation process in which a traction apparatus in the present application is used to stretch and separate a mucosa is described by using an example in which the traction portion is merely composed of a closed traction structure. During an actual operation process, an electric knife may be inserted nearby a tissue having a lesion through a biopsy channel of an endoscope, making marks around a position having a lesion. After the marks are made, liquid is injected though the electric knife or an external syringe, so that the tissue having a lesion swells, and a liquid buffer layer, that is, a "water cushion", is formed under the mucosa.

As shown in FIG. 2 to FIG. 6, FIG. 2 is a schematic diagram showing the cooperating of a clip portion 2 and a traction portion 1 with each other. The clip portion 2 includes clip main bodies 23 and 25 and clip arms 24 and 26. After the mucosa is pre-separated within the body, the electric knife is taken out, and the clip arm 24 of the clip portion 2 of the traction apparatus is enabled. The clip arm 24 clips one end of the closed traction structure 11 of the traction portion 1.

Figure 3:
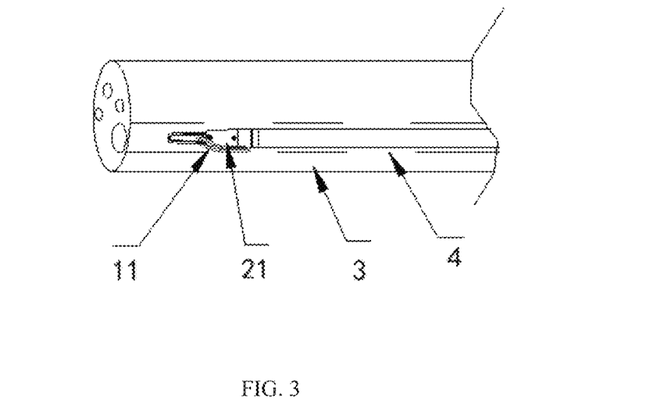
FIG. 3 is a schematic diagram of entering a clip portion and a traction portion into a biopsy channel of an endoscope.
Figure 4:
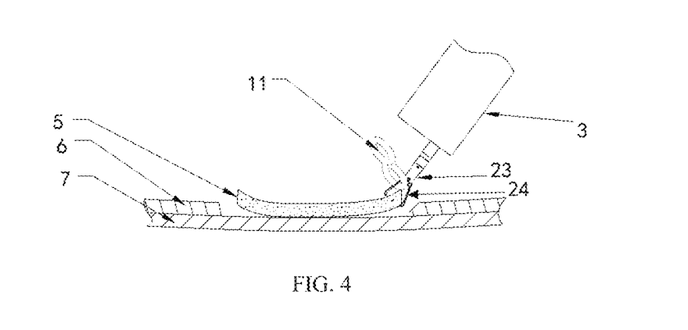
FIG. 4 is a schematic diagram of clip a nidus by using a first clip portion and an annular closed traction structure under guidance of an endoscope.

As shown in FIG. 3 and FIG. 4, after a first clip portion 21 and the closed traction structure 11 are placed in a biopsy channel 4 of an endoscope 3 and reach the distal end of the biopsy channel 4, by observing from an eye lens of the endoscope 3, the clip arm 24 of the first clip portion 21 is opened to clip one side of the pre-separated nidus 5 and one end of the closed traction structure 11 at the same time. At this time, a proximal end and a distal end of the main clip body 23 of the first clip portion 21 are separated, so that the distal end of the main clip body of the first clip portion 21 and the closed traction structure 11 are left in the body, and the main clip body 23 is taken out.

Figure 5:
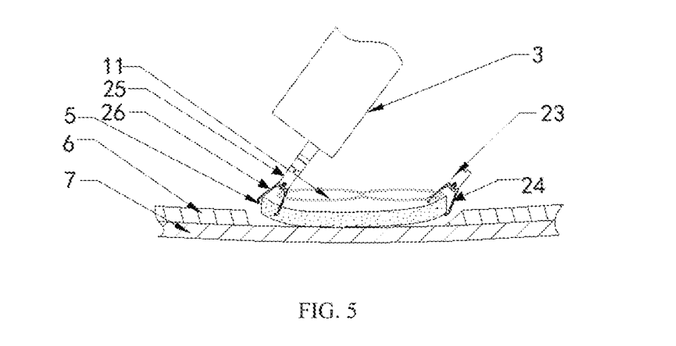
FIG. 5 is a schematic diagram of clip a nidus by using a second clip portion and an annular closed traction structure under guidance of an endoscope.

As shown in FIG. 5, after a second clip portion 22 is inserted into the biopsy channel 4 of the endoscope and reaches the distal end of the biopsy channel 4, by observing from the eye lens of the endoscope 3, a clip arm 26 of the second clip portion 22 is opened to clip the other end of the closed traction structure 11, and to stretch to the other side of the pre-separated nidus 5 under the guidance of the endoscope. Subsequently, the proximal end and the distal end of the main clip body 25 of the second clip portion 22 are separated, so that the distal end of the main clip body of the second clip portion 22 and the closed traction structure 11 are left in the body.

Figure 6:
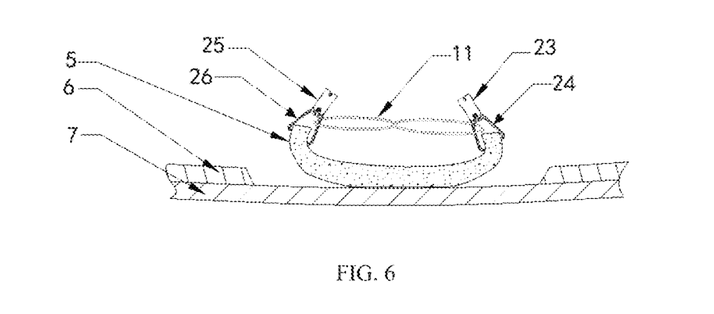
FIG. 6 is a schematic diagram of separating a nidus by a clip portion and an annular closed traction structure cooperating with each other.

Because the closed traction structure 11 is elastic, during a cutting process of an operation, the cut nidus 5 is everted due to elastic force of the traction portion 1. With progress of a cutting operation, the cut nidus 5 is constantly pulled up to be gradually separated from a muscular layer 7, until being completely pulled up. In this way, the nidus 5 is completely separated. According to such a traction manner, the nidus 5 is cut and is everted at the same time, thereby widening the surgical field. A blood vessel under the mucosa may be found when looking directly from the endoscope, and bleeding may be avoided. In this way, the operation becomes more convenient and safer, and the operation time is shortened.

If the nidus 5 is too large, the number of clip portions 2 and closed traction structures may be increased, so that the cut nidus 5 is completely pulled up; or as shown in FIG. 8, the traction portion 1 having an elastic linear structure may be selected, so that the range of elastic deformation of the entire traction portion 1 is increased to stretch a nidus 5 with a relatively large area.

Figure 7:
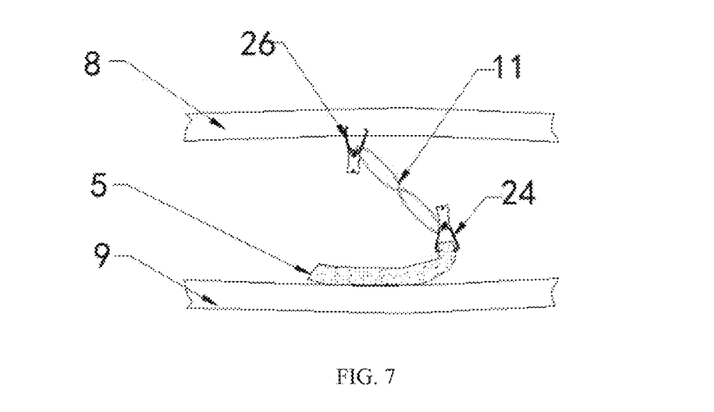
FIG. 7 is a schematic diagram of separating a nidus in a narrow space by using a traction apparatus.

As shown in FIG. 4 and FIG. 7, when the nidus 5 is relatively large while the space is relatively small, for example, an ESD operation is performed in an intestine, one side of the nidus 5 may be cut first. As shown in FIG. 4, the nidus 5 is clipped by using the clip arm 24 of the first clip portion 21. The second clip portion 22 is fed in by the endoscope 3. By observing from the eye lens of the endoscope 3, the clip arm 26 of the second clip portion 22 clips a mucosa layer 8 at an opposite side of an intestinal canal. The clip arm 26 of the second clip portion 22 is closed. Under of the action of elastic force of the closed traction structure 11, the cut nidus 5 is constantly pulled up with progress of the cutting operation, thus keeping the surgical field and facilitating the operation.

Figure 9A:
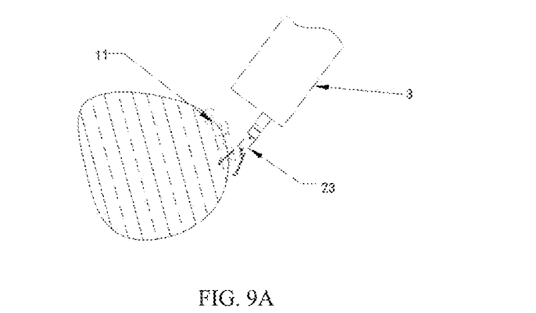
FIG. 9A to FIG. 9C are schematic diagrams of reducing a wound surface of a nidus by using a traction apparatus when the wound surface of the nidus is relatively large.
Figure 9B:
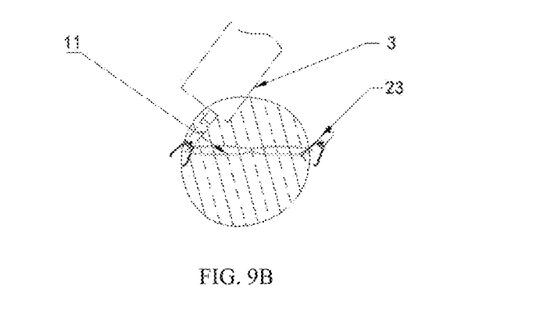
Figure 9C:
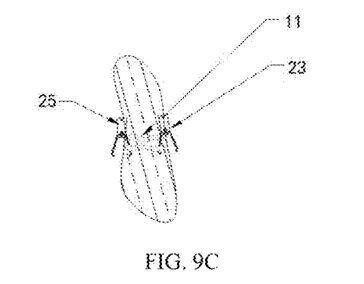

As shown in FIG. 9A to FIG. 9C, when a wound surface of the nidus 5 is relatively large, the observation and guidance operation is performed by the endoscope 3. One side of the wound surface of the nidus 5 and one end of the closed traction structure 11 are clipped first by using the clip arm 24 of the first clip portion. The other side of the wound surface of the nidus 5 and the other end of the closed traction structure 11 are further clipped by using the clip arm 26 of the second clip portion. Due to the elastic force of the closed traction structure 11, both sides of the wound surface of the nidus 5 are pulled inward, so that the wound surface of the nidus 5 is reduced. In this way, the wound surface of the nidus 5 is further closed by clip.

Figure 10:
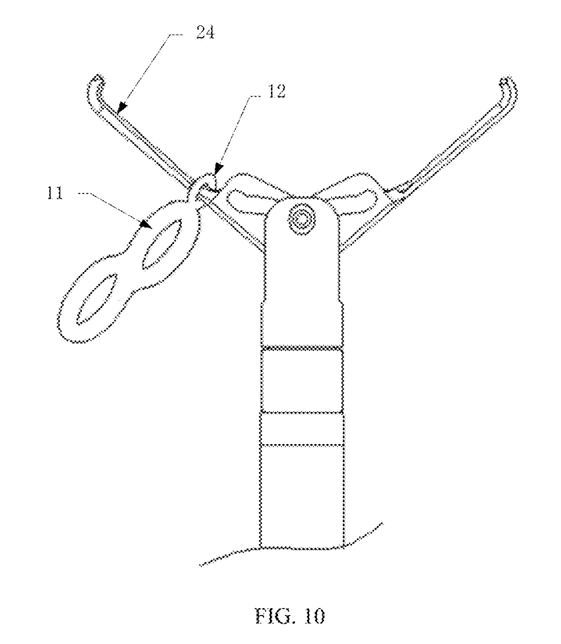
FIG. 10 is a schematic diagram of the structure of the traction portion with connection ring.

In some embodiments of the present application, as shown in FIG. 10, the traction portion 1 further includes a connection ring 12, which is a ring structure arranged on the outer edge position of the closed traction structure 11. The connection ring 12 may be sleeved on the clip arm 24, and therefore, the inner space area of the connection ring 12 is smaller compared with the more convenient and safer closed traction structure 11.

For example, when the closed traction structure 11 is a round structure, the inner diameter of the connection ring 12 shall be smaller than the diameter of the circle formed by the closed traction structure 11. During the actual application, the closed traction structure 11 with a larger inner area generates the main elastic force action, and in this way such a structure may realize the traction of the wound tissue. On the other hand, the connection ring 12 with a smaller inner area is sleeved on the clip arm 24, so that the traction portion 1 is not easy to drop off from the clip arm 24 when the traction portion 1 is moved in the surgical area and in the endoscope channel driven by the clip arm 2, and the surgical success rate is improved.

The connection ring 12 may be made of elastic material, so that the connection ring 12 is able to be sleeved on the clip arm 24 by using the elasticity of the connection ring 12. In some embodiments, the inner diameter of the connection ring 12 is smaller than or equals to the width of the clip arm 24 so as to be closely sleeved on the clip arm, so that the connecting stability is improved.

The width of the clip arm refers to total width of the clip arm 24 at the thinnest position. The physical quantity referred to by the width of the clip arm 24 is different according to different shape of the clip arm 24. For example, when the cross-section shape of the clip arm 24 is rectangular, the width of the clip arm 24 refers to the length of long side of the rectangle. When the cross-section shape of the clip arm 24 is circular, the width of the clip arm 24 refers to the diameter of the circle. When the cross-section shape of the clip arm 24 is polygonal, the width of the clip arm 24 refers to the diagonal line of the cross polygon or the distance between two most distant vertices.

When the inner diameter of the connection ring 12 is smaller than or equals to the width of the clip arm 24, the connection ring 12 may be expanded when the connection ring is sleeved on the clip arm 24, so that the connection ring 12 is deformed and an elastic force for shrinking the connection ring 24 inward is generated. By the elastic force of the connection ring 12, the connection ring 12 may be closely sleeved on the clip arm 24, which increases the frictional force between the contact surfaces of the connection ring 12 and the clip arm 24, so that the connection ring 12 is not easy to slide on the clip arm 24, increasing the connection stability between the traction portion 1 and the clip portion 2.

Additionally, the clip arm 24 is generally made of a hard material such as metal, while the elastic material making the connection ring 12 is generally a soft material such as silicon rubber. Therefore, the frictional coefficient between the hard material and the soft material is large, which further increases stability. In some embodiments, the connection ring 12 may be made of an elastic material the same as the material of the closed traction structure 11, and may be formed an integral structure with the closed traction structure 11 so as to facilitate the forming processes.

During an actual surgical procedure, by sleeving the connection ring 12 on the clip arm 24 and driving the traction portion 1 through the endoscope channel by the clip portion 2, the traction portion 1 may be delivered to the operation position. Therefore, the connection ring 12 may be sleeved on the clip arm 24 only before delivering it to the surgical area. That is, the connection ring 12 may be arranged on an outer edge position at one side of the closed traction structure 11. During the surgical process, the connection ring 12 may be sleeved on the clip arm 24 at one side, and is delivered to the surgical area; while on the other side, the traction to the tissue may be realized by directly clipping the closed traction structure 11 with the clip arm 24. Because the inner area of the closed traction structure 11 is larger, it is convenient for completing the clipping operation at the surgical area.

Moreover, in order to further increase the stability of the connection position, the shape of the inner side of the connection ring 12 may be adapted to the shape of clip arm 24 or the shape of a part of the clip arm 24. That is, the shape of the inner area of the connection ring 12 is the same as the cross-section shape of the clip arm 24. For example, the connection ring 12 is a circular ring structure, and the cross-section shape of the clip arm 24 is circular. The shape of the inner area of the connection ring 12 is rectangular, and the cross-section shape of the clip arm 24 is also rectangular. By the adaptive shapes, the contact area between the inner side of the connection ring 12 and the outer surface of the clip arm 24 may be increased, which is favorable for maintaining the connection stability. Moreover, after the closed traction structure 11 is deformed by stretching, the adaptive shapes may relieve the reverse between the connection ring 12 and clip 24, further increasing the stability of the connection position.

As a cooperative action member, the structure of the clip portion 2 should be suitable for maintaining connection stability. For example, the two clip arms 24 of the clip portion 2 may be arranged symmetrically on the same pivot shaft, and when the two arms 24 are closed. A closed ring area is formed for clipping tissues and making the traction portion 1 be clipped between the two arms, avoiding the dropping off of the traction portion 1 from the inside of the two clip arms 24.

For example, a guiding groove is arranged in the area close to the pivot shaft and on the two clip arms 24 of the clip portion 2. The guiding groove may be formed as a corner-shaped structure, wherein in the direction from the proximal end to the distal end, the groove has a preset inclination angle with respect to the extending direction of the clip arm 24 first, and then gradually becomes parallel (or nearly parallel) with respect to the extending direction of the clip arm 24, and has a depth in the direction parallel (or nearly parallel) to the extending direction of the clip arm 24. A pivot shaft is arranged in the guiding groove. During the surgical proceeding, the pivot shaft may move in the guiding groove. When the pivot shaft moves at the inclination position, the two clip arms 24 gradually open or close. When the pivot shaft moves at the parallel (or nearly parallel) position, the two clip arms are in a completely closed state, and the closed state is locked by preset distance in depth, so that the two clip arms are maintained in a stable closed state, avoiding the drop off of the traction portion 1 from the two clip arms.

Figure 11:
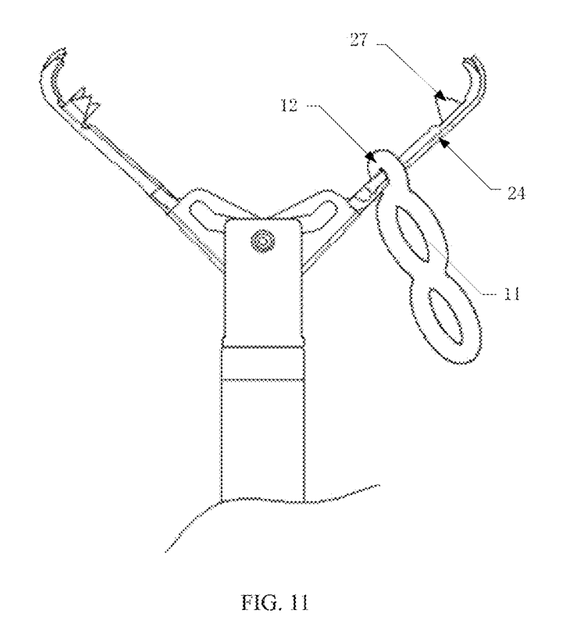
FIG. 11 is a schematic diagram of the structure of the clip portion with inner thorns.

In some embodiments of the present application, the clip portion further includes inner thorns. As shown in FIG. 11, the inner thorn 27 may be provided at any position between two ends of the clip arms 24 according to operation requirements. For example, the inner thorn may be provided at the position close to the distal end of the clip arm 24, so that when the clip arms 24 clip tissues, the inner thorn may also be able to clip a part of the tissues, making the clip process more stable. The inner thorn 27 may be provided protrusively on the clip arm 24 towards the clipping direction of the clip arm 24, so as to avoid the sliding of the traction portion 1 on the clip arm 24.

The traction portion 1 is most easy to drop off from the distal end of the two clip arms 24. When the inner thorn 27 is provided protrusively on the clip arm 24, the inner thorn 27 may block the traction portion 1 in the direction that the traction portion 1 slides to the distal end, which further relieves the drop off of the traction portion 1 from the clip arm 24.

In some embodiments, the distal ends of two clip arms 24 may be provided with serrated structures matching each other. The structures matching each other enable the distal ends of the two clip arms 24 to enter each other a distance, so that the tissues may be clipped between the two clip arms 24. Correspondingly, the inner thorns 27 on the two clip arms 24 may also be provided serrated structures matching each other. For example, the inner thorn 27 on one clip arm 24 is provided with convex teeth, while the inner thorn 27 on the other clip arm 24 is provided concave teeth, wherein the two structures match each other to form a closed area, avoiding the traction portion 1 from dropping off from the two clip arms 24.

Merely preferable implementations of this application are described above, so that a person skilled in the art can understand or implement the invention of this application. Various modifications to these embodiments and combinations of these embodiments are obvious to a person skilled in the art. General principles defined in this specification may be achieved in other embodiments without departing from the spirit or scope of this application. Therefore, this application would not be limited to these embodiments shown in this specification, but should be conform to a widest scope consistent with the principle and novelty features disclosed in this specification.

What is claimed is:

1. A traction apparatus, wherein the traction apparatus comprises a clip portion and a traction portion; the traction portion contains a closed traction structure; the closed traction structure is made of an elastic material; the clip portion comprises a main clip body and a clip arm; the main clip body is capable of passing through a biopsy channel of an endoscope; and the clip arm is capable of clipping one end of the closed traction structure and one end of a pre-separated nidus, wherein the closed traction structure comprises two or more closed traction structures, wherein at least two of the closed traction structures act for everting cut nidus during a cutting process of an operation, such that the cut nidus is pulled up by elastic force of the closed traction structures to complete tissue separation, wherein the traction portion further comprises a connection ring which is a ring structure arranged on an outer edge position of the closed traction structure, configured to be sleeved on the clip arm.

2. The traction apparatus according to claim 1, wherein the closed traction structure is made of silicon rubber or a thermoplastic elastomer.

3. The traction apparatus according to claim 1, wherein an elastic connection structure is provided between the two or more closed traction structures.

4. The traction apparatus according to claim 3, wherein the elastic connection structure is an elastic linear structure.

5. The traction apparatus according to claim 3, wherein the elastic connection structure is an elastic ring structure.

6. The traction apparatus according to claim 1, wherein the closed traction structure is a combination of one or more of round shape, triangular shape, rhombic shape, or square shape.

7. The traction apparatus according to claim 1, wherein the closed traction structure is capable of being elastically deformed by moving the main clip body of the clip portion.

8. The traction apparatus according to claim 1, wherein the inner diameter of the connection ring is smaller than or equals to the width of the clip arm so as to be sleeved on the clip arm closely to improve the connecting stability.

9. The traction apparatus according to claim 1, wherein the connection ring is arranged on the outer edge position at one side of the closed traction structure.

10. The traction apparatus according to claim 1, wherein the clip portion further comprises inner thorns, which is provided protrusively on the clip arm towards the clipping direction of the clip arm to avoid the sliding of the clip portion on the clip arm.

11. The traction apparatus according to claim 10, wherein ends of the inner thorns arranged on two clip arms that open and close towards each other are provided with serrated structures matching each other.

12. A traction ring used for a traction apparatus, wherein the traction ring is formed by connecting two or more closed traction structures, and the traction ring is made of an elastic material, wherein at least two of the closed traction structures act for everting cut nidus during a cutting process of an operation, such that the cut nidus is pulled up by elastic force of the closed traction structures to complete tissue separation, wherein the traction portion further comprises a connection ring which is a ring structure arranged on an outer edge position of the closed traction structure, configured to be sleeved on the clip arm.

13. The traction ring according to claim 12, wherein an elastic connection structure is provided between two or more closed traction structures.

14. The traction ring according to claim 13, wherein the elastic connection structure is an elastic linear structure.

15. The traction ring according to claim 13, wherein the elastic connection structure is an elastic ring structure.

16. The traction ring according to claim 12, wherein the closed traction structure is a combination of one or more of round shape, triangular shape, rhombic shape, or square shape.

17. The traction ring according to claim 12, wherein the inner diameter of the connection ring is smaller than or equals to the width of the clip arm so as to be sleeved on the clip arm closely to improve the connecting stability.

18. The traction ring according to claim 12, wherein the connection ring is arranged on an outer edge at one side of the closed traction structure.

* * * * *